United States Patent
Nakatsuji (10) Patent No.: US 9,918,697 B2
(45) Date of Patent: Mar. 20, 2018

(54) ULTRASOUND OBSERVATION APPARATUS

(71) Applicant: OLYMPUS CORPORATION, Tokyo (JP)

(72) Inventor: Tomohiro Nakatsuji, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/422,616

(22) Filed: Feb. 2, 2017

(65) Prior Publication Data

US 2017/0143301 A1 May 25, 2017

Related U.S. Application Data

(63) Continuation of application No. PCT/JP2015/075328, filed on Sep. 7, 2015.

(30) Foreign Application Priority Data

Oct. 16, 2014 (JP) .................. 2014-211786

(51) Int. Cl.
- *A61B 8/14* (2006.01)
- *A61B 8/08* (2006.01)
- *A61B 8/00* (2006.01)

(52) U.S. Cl.
CPC .............. *A61B 8/14* (2013.01); *A61B 8/4254* (2013.01); *A61B 8/463* (2013.01); *A61B 8/469* (2013.01);
(Continued)

(58) Field of Classification Search
CPC ......... A61B 8/14; A61B 8/4254; A61B 8/463; A61B 8/469; A61B 8/5207; A61B 8/5269; A61B 8/54
See application file for complete search history.

(56) References Cited

U.S. PATENT DOCUMENTS

2004/0159155 A1 8/2004 Ogasawara
2008/0262354 A1 10/2008 Yoshida et al.
(Continued)

FOREIGN PATENT DOCUMENTS

JP 2003-061959 A 3/2003
JP 2007-330764 A 12/2007
(Continued)

OTHER PUBLICATIONS

International Search Report dated Dec. 1, 2015 issued in PCT/JP2015/075328.
(Continued)

*Primary Examiner* — Michael Rozanski
(74) *Attorney, Agent, or Firm* — Scully, Scott, Murphy & Presser, P.C.

(57) ABSTRACT

An ultrasound observation apparatus includes: an ultrasound probe; a transmitting-receiving section; an image processing section; an input section; a reference image storage section; a first position correction section; a movie storage section; a TIC analysis section; a second position correction section; a sensor; and a positional information storage section, wherein the first position correction section automatically corrects, based on information of a position and direction of the ultrasound probe, a scanning plane to allow a reference image to be constantly displayed, the second position correction section automatically corrects a position of second region of interest, based on the information of the position and direction of the ultrasound probe, and the transmitting-receiving section controls an output of ultrasound beam to allow an output of ultrasound beam in acquisition of temporal variation data of contrast luminance to be larger than an output of ultrasound beam in acquisition of volume data.

5 Claims, 6 Drawing Sheets

(52) U.S. Cl.
 CPC .......... *A61B 8/5207* (2013.01); *A61B 8/5269* (2013.01); *A61B 8/54* (2013.01)

(56) References Cited

U.S. PATENT DOCUMENTS

| | | |
|---|---|---|
| 2011/0230765 A1 | 9/2011 | Guracar |
| 2013/0096430 A1 | 4/2013 | Yoshiara et al. |

FOREIGN PATENT DOCUMENTS

| | | |
|---|---|---|
| JP | 2011-194228 A | 10/2011 |
| JP | 4801229 B2 | 10/2011 |
| JP | 2011-254963 A | 12/2011 |
| JP | 2013-081764 A | 5/2013 |

OTHER PUBLICATIONS

Japanese Office Action dated Apr. 5, 2016 issued in JP 2016-501479.

ULTRASOUND OBSERVATION APPARATUS

CROSS REFERENCE TO RELATED APPLICATION

This application is a continuation application of PCT/JP2015/075328 filed on Sep. 7, 2015 and claims benefit of Japanese Application No. 2014-211786 filed in Japan on Oct. 16, 2014, the entire contents of which are incorporated herein by this reference.

BACKGROUND OF THE INVENTION

1. Field of the Invention

The present invention relates to an ultrasound observation apparatus, and in particular, to an ultrasound observation apparatus that can calculate temporal variation of luminance in a region of interest.

2. Description of the Related Art

An ultrasound observation apparatus has been widely used in a medical field or other fields. The ultrasound observation apparatus transmits and receives ultrasound to/from a subject to generate an ultrasound image that indicates acoustic characteristics inside the subject, and uses the ultrasound image in inspection and diagnosis of the subject.

The ultrasound observation apparatus used in the medical field or other fields includes an ultrasound probe that is capable of transmitting and receiving ultrasound to/from the subject, and generates a B-mode image that is a cross-sectional image of the subject. The B-mode image is obtained through scanning of a predetermined scanning plane with an ultrasound beam.

For example, Japanese Patent No. 4801229 discloses an ultrasound observation apparatus that acquires volume data of a B-mode image, and then calculates correlation in all scanning planes to constantly display an optimum scanning plane (having the highest correlation) in order for continuous favorable observation of a treatment using treatment instruments without deviation from the scanning plane.

Also, such an ultrasound observation apparatus uses TIC (time intensity curve) analysis as an objective diagnostic approach using an ultrasound contrast agent. In the TIC analysis, a region of interest (ROI) for TIC analysis is set to a region of interest in the scanning plane, and temporal variation of contrast luminance in the ROI is calculated.

For example, Japanese Patent Application Laid-Open Publication No. 2011-254963 discloses an ultrasound diagnostic apparatus that generates luminance time curves of at least one analysis region with, as a scanned region, a two-dimensional region or a three-dimensional region including a predetermined site of a subject medicated with a contrast agent, then analyzes a retention time period of the contrast agent in the analysis region to display different color phase that is assigned dependently on the retention time period.

SUMMARY OF THE INVENTION

An ultrasound observation apparatus according to an aspect of the present invention sets a second region of interest for analysis of temporal variation of luminance to a first region of interest and calculates the temporal variation of the luminance in the second region of interest. The ultrasound observation apparatus includes: an ultrasound probe configured to change a transmitting-receiving direction of ultrasound in a first direction and a second direction to perform two-dimensional scanning with an ultrasound beam; a transmitting-receiving section configured to control the transmitting-receiving direction of the ultrasound beam of the ultrasound probe; an image processing section configured to generate volume data of a B-mode image from a result of scanning with the ultrasound beam in the first direction and the second direction; an input section configured to set, as a reference image, an image in which the first region of interest is clearly visualized; a reference image storage section configured to hold the reference image; a first position correction section configured to correct a scanning plane to allow an image of the volume data similar to the reference image that is set by the input section, to be constantly displayed; a movie storage section configured to hold a movie obtained by transmitting and receiving the ultrasound beam to/from only the scanning plane that is corrected by the first position correction section; a TIC analysis section configured to calculate temporal variation of contrast luminance in the second region of interest that is set to the first region of interest; a second position correction section configured to automatically correct the position of the second region of interest for TIC analysis, in synchronization with movement of the first region of interest in the scanning plane held by the movie storage section; a sensor provided in the ultrasound probe, and configured to detect a position and a direction of the ultrasound probe; and a positional information storage section configured to hold information of the position and the direction of the ultrasound probe detected by the sensor. The first position correction section automatically corrects, based on the information of the position and the direction of the ultrasound probe that is read from the positional information storage section, the scanning plane to allow the reference image held by the reference image storage section to be constantly displayed. The second position correction section automatically corrects the position of the second region of interest, based on the information of the position and the direction of the ultrasound probe that is read from the positional information storage section. The transmitting-receiving section further controls an output of the ultrasound beam to allow an output of the ultrasound beam in acquisition of temporal variation data of the contrast luminance to be larger than an output of the ultrasound beam in acquisition of the volume data.

DETAILED DESCRIPTION OF THE PREFERRED EMBODIMENT(S)

Hereinafter, embodiments of the present invention are described with reference to drawings.

First Embodiment

Figure 1:
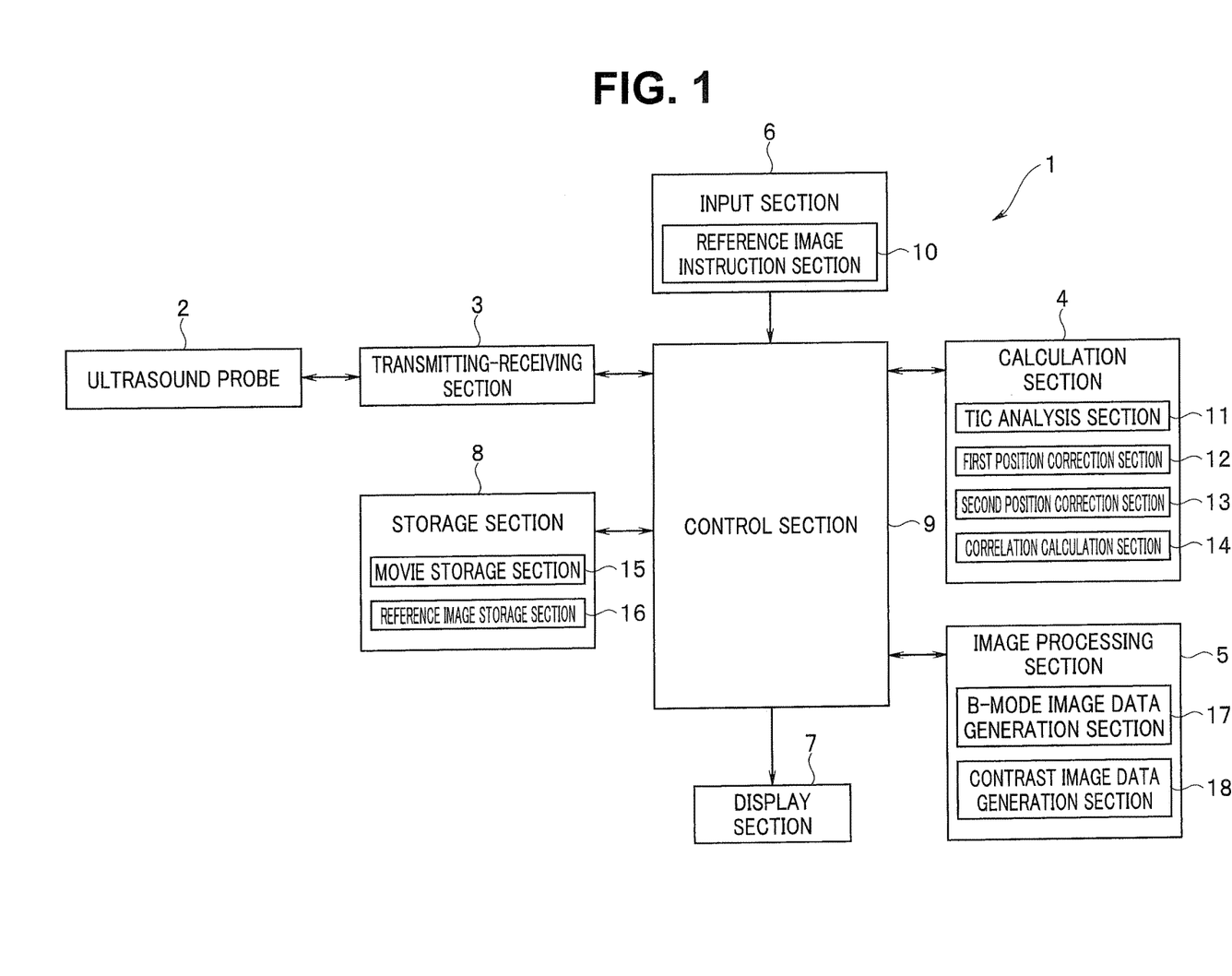
FIG. 1 is a block diagram illustrating an entire configuration of an ultrasound observation apparatus according to a first embodiment.

First, a configuration of an ultrasound observation apparatus according to a first embodiment is described with reference to FIG. 1. FIG. 1 is a block diagram illustrating an entire configuration of an ultrasound observation apparatus according to the first embodiment. An ultrasound observation apparatus 1 illustrated in FIG. 1 is an apparatus used to observe a subject with use of ultrasound.

The ultrasound observation apparatus 1 includes: an ultrasound probe 2 that outputs an ultrasound pulse to the subject and receives an ultrasound echo reflected by the subject; a transmitting-receiving section 3 that transmits and receives an electric signal to/from the ultrasound probe 2; a calculation section 4 that performs predetermined calculation on an electric echo signal that is converted from the ultrasound echo; an image processing section 5 that generates image data corresponding to the electric echo signal converted from the ultrasound echo; an input section 6 that is configured of interfaces such as a keyboard, a mouse, and a touch panel, and receives input of various kinds of information; a display section 7 that is configured of a display panel formed of a liquid crystal, an organic EL or the like, and displays various kinds of information including the image that is generated by the image processing section 5; a storage section 8 that holds various kinds of information including an image and a movie acquired from the subject; and a control section 9 that controls entire operation of the ultrasound observation apparatus 1.

The ultrasound probe 2 is configured to perform two-dimensional scanning with an ultrasound beam by changing a transmitting-receiving direction in a first direction and a second direction with use of an ultrasound transducers that are two-dimensionally arranged. The ultrasound probe 2 converts an electric pulse signal received from the transmitting-receiving section 3, into an ultrasound pulse, and converts an ultrasound echo that is reflected by an outside subject, into an electric echo signal again.

The transmitting-receiving section 3 is electrically connected with the ultrasound probe 2, and transmits the pulse signal to the ultrasound probe 2 and receives the echo signal from the ultrasound probe 2. More specifically, the transmitting-receiving section 3 generates the pulse signal based on a preset waveform and preset transmission timing, and transmits the generated pulse signal to the ultrasound probe 2. Also, the transmitting-receiving section 3 performs processing such as amplification and filtering on the received echo signal, and then performs A/D conversion, thereby generating a digital signal to provide the digital signal to the control section 9.

The input section 6 includes a reference image instruction section 10 that sets, as a reference image, an image in which a region of interest is clearly visualized, in order to perform TIC (time intensity curve) analysis. The reference image is previously fabricated by a user according to the size of the region of interest, clarity of a contour of the region of interest, and the like. Note that the setting of the reference image is not limited to the reference image instruction section 10, and for example, a reference image setting button may be provided, or the setting of the reference image may be linked to an unillustrated movie recording button.

The image processing section 5 includes: a B-mode image data generation section 17 that generates B-mode image data; and a contrast image data generation section 18 that generates contrast image data with use of a signal reflected by a contrast agent flowing into the subject. The B-mode image data displays luminance that is converted from an amplitude of the echo signal.

The data generated by the B-mode image data generation section 17 is volume data. Note that ultrasound power (an MI value) in acquisition of the volume data may be controlled to minimize destruction of the contrast agent.

The storage section 8 includes: a movie storage section 15 that holds the contrast image data (a movie); and a reference image storage section 16 that holds the reference image set by the reference image instruction section 10. The contrast image data is acquired with use of a signal from the contrast agent that is administered to and flows into the subject.

The movie storage section 15 holds a movie of an optional plane of the volume data in which the region of interest is displayed, in order to suppress data capacity. The volume data of the B-mode image generated by the B-mode image data generation section 17 is not stored in the movie storage section 15 and is used only for calculation to correct the position of the scanning plane.

The calculation section 4 includes: a TIC analysis section 11 that performs TIC analysis; a first position correction section 12 that corrects deviation of the scanning plane with respect to movement of the region of interest for TIC analysis; a second position correction section 13 that performs contour extraction of the region of interest in the scanning plane to automatically correct the position of a ROI for the TIC analysis, in synchronization with the movement of the region of interest in the scanning plane; and a correlation calculation section 14 that calculates a correlation value between the volume data of the B-mode image generated by the B-mode image data generation section 17 and the reference image held by the reference image storage section 16.

The first position correction section 12 calculates the correlation between the acquired volume data and the reference image, and moves the scanning plane in the second direction of the transmitting-receiving section 3 in order to display, on the display section 7, the scanning plane having the largest correlation value. More specifically, the first position correction section 12 corrects the scanning plane such that an image similar to the reference image set by the input section 6 is constantly displayed. A method of determining the optimum scanning plane is described later.

To calculate the correlation between the acquired volume data and the reference image, image processing so-called pattern matching is performed on the generated B-mode image with use of the reference image as a template, and calculates similarity between the echo pattern in the B-mode image and the reference image. The image processing may be, for example, pattern matching of the contour of the region of interest, or pattern matching of adjacent organs displayed on the image. The correlation value becomes high as the similarity between the echo pattern in the B-mode image and the reference image is higher. Note that the detailed description of the pattern matching is omitted because the pattern matching is a well-known technology.

Note that, when the ultrasound power (the MI value) is suppressed in order to minimize destruction of the contrast agent in acquisition of the volume data, the ultrasound is applied to the optimum plane (the scanning plane having the largest correlation) with the ultrasound power that is the same as the ultrasound power in acquisition of the normal B-mode image and the contrast imaging mode image.

The second position correction section 13 uses, as the template, the region of interest in the scanning plane image determined by the first position correction section 12, and uses the above-described pattern matching processing, thereby automatically correcting the position of the ROI for TIC analysis, in synchronization with the movement of the region of interest.

Figure 2:
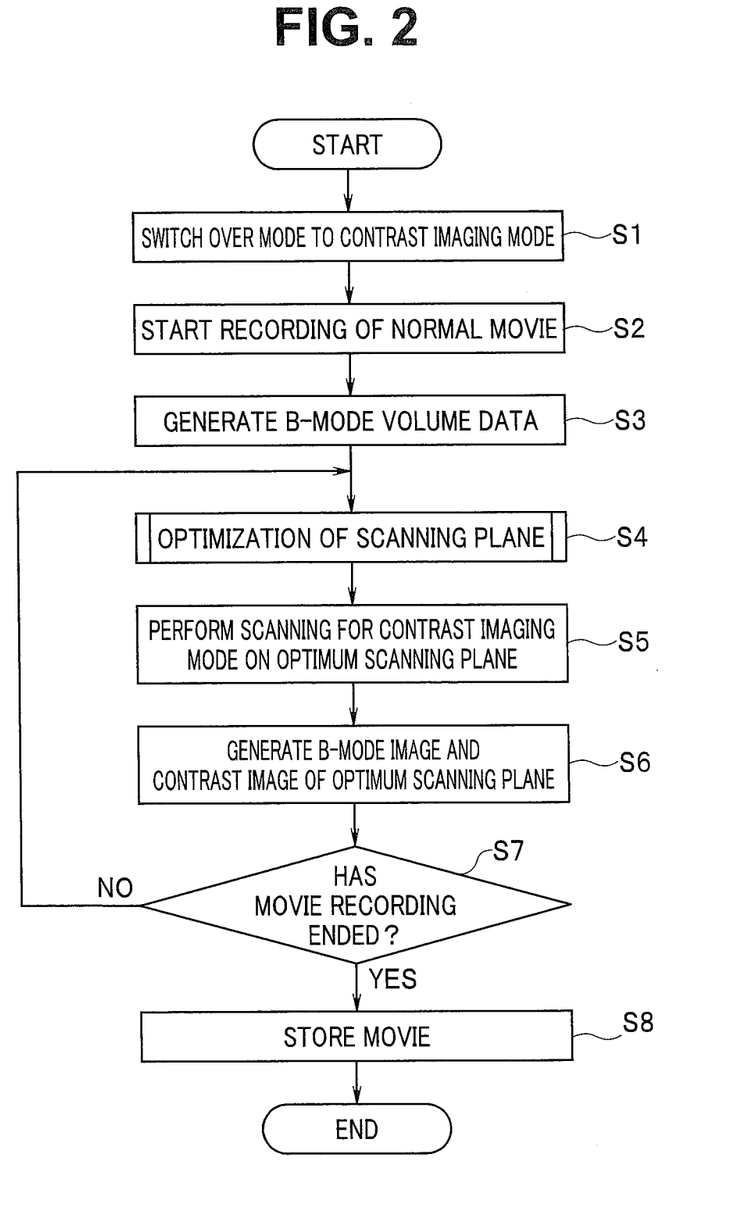
FIG. 2 is a flowchart for explaining an example flow of processing in a case where TIC analysis is not performed.

Next, operation of the ultrasound observation apparatus 1 having the above-described configuration is described. First, the operation in a case where the TIC analysis is not performed is described. FIG. 2 is a flowchart for explaining an example flow of the processing in the case where the TIC analysis is not performed.

When operation of releasing a frozen state is inputted through the input section 6, the ultrasound echo is transmitted and received by the ultrasound probe 2, and measurement is accordingly started. First, the mode is switched over to the contrast imaging mode (step S1), and recording of a normal movie is started (step S2) when operation of starting the movie recording is inputted through the input section 6.

The volume data of the B-mode image is generated from the ultrasound echo that is received by the ultrasound probe 2, by the image processing section 5 (step S3). Note that the ultrasound power (the MI value) in acquisition of the volume data may be controlled to minimize destruction of the contrast agent.

Next, optimization of the scanning plane is performed by the first position correction section 12 (step S4). In the process in step S4, the correlation between the volume data and the reference image is calculated, the scanning plane having the highest correlation is set to the optimum scanning plane, and the image of the set scanning plane is continuously displayed.

The scanning for contrast imaging mode is performed on the optimum scanning plane (step S5). In other words, in the process in step S5, the ultrasound echo to acquire the B-mode image and the contrast imaging mode image is transmitted only to the optimum scanning plane. Next, the B-mode image and the contrast image are generated from the ultrasound echo by the image processing section 5 (step S6).

Next, it is determined whether operation of terminating the movie recording has been performed through the input section 6 (step S7). When it is determined that the operation of terminating the movie recording has not been performed (No in step S7), the process returns to step S4, and the similar process is repeated. On the other hand, when it is determined that the operation of terminating the movie recording has been performed (Yes in step S7), the movie recording is terminated, the movie is stored (step S9), and the process is completed.

Figure 3:
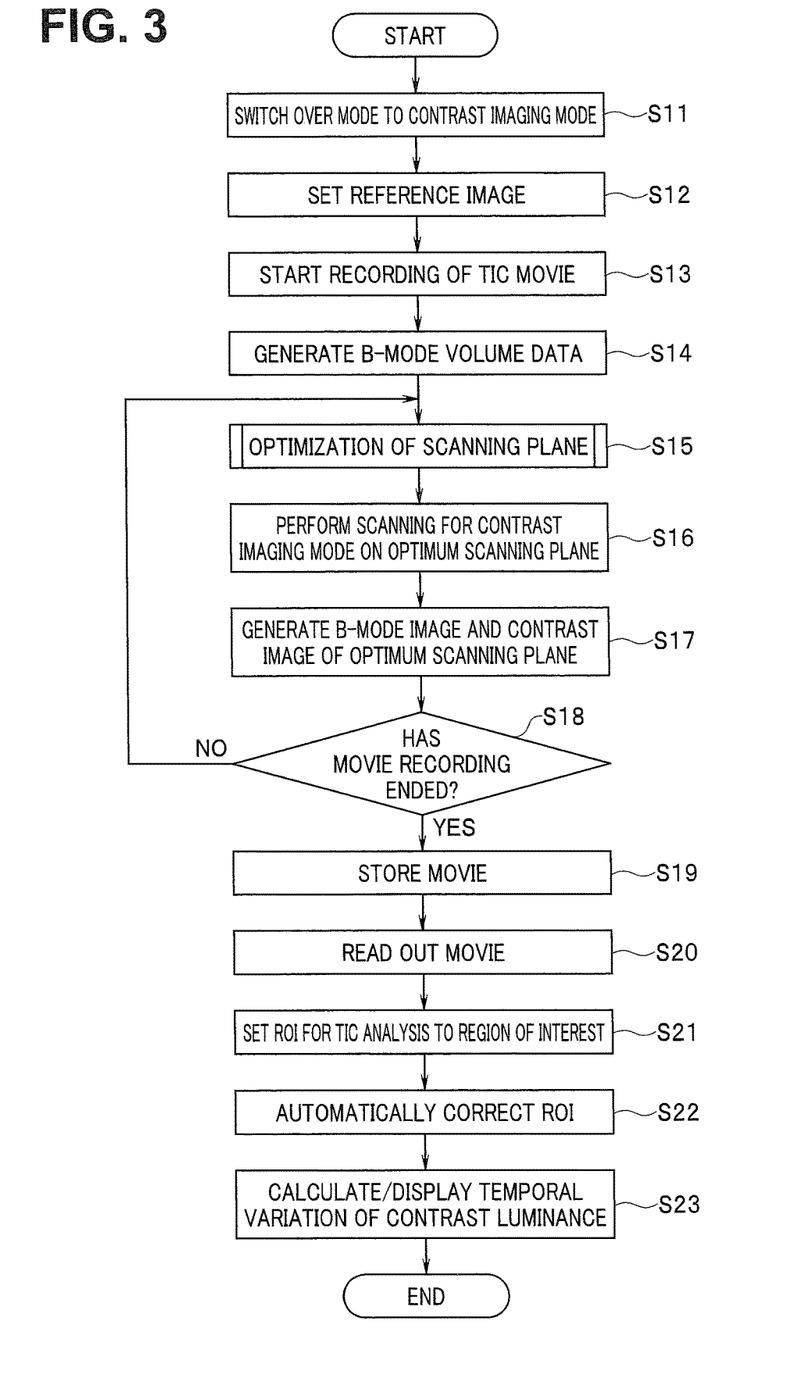
FIG. 3 is a flowchart for explaining an example flow of processing in a case where TIC analysis is performed.

Next, the operation in a case where the TIC analysis is performed is described. FIG. 3 is a flowchart for explaining an example flow of the processing in the case where the TIC analysis is performed.

When the operation of releasing the frozen state is inputted through the input section 6, the ultrasound probe 2 transmits and receives the ultrasound echo, thereby starting the measurement. First, the mode is switched over to the contrast imaging mode (step S11), and the reference image is set (step S12). When the TIC analysis is performed, the image in which the region of interest, temporal variation of the contrast luminance of which is desired to be known, is clearly visualized is previously set by the reference image instruction section 10. Note that the process in step S12 may be performed in conjunction with the movie recording in step S13. The set reference image is stored in the reference image storage section 16.

When operation of starting the movie recording is inputted through the input section 6, recording of the movie is started (step S13). The volume data of the B mode image is generated, by the image processing section 5, from the ultrasound echo that has been received by the ultrasound probe 2 (step S14). Note that the ultrasound power (the MI value) in acquisition of the volume data may be controlled in order to minimize destruction of the contrast agent.

Optimization of the scanning plane is performed by the first position correction section 12 (step S15). In the process in step S15, the correlation between the volume data and the reference image is calculated, the scanning plane having the highest correlation is set to the optimum scanning plane, and the image of the set scanning plane is continuously displayed.

The ultrasound echo to acquire the B-mode image and the contrast image is transmitted only to the optimum scanning plane (step S16). The ultrasound echo to be transmitted is applied with the ultrasound power (the MI value) that is the same as the ultrasound power in acquisition of the normal B-mode image and the contrast imaging mode image.

The B-mode image and the contrast image are generated from the ultrasound echo by the image processing section 5 (step S17). It is determined whether the operation of terminating the movie recording has been performed through the input section 6 (step S18). When it is determined that the operation of terminating the movie recording has not been performed (No in step S18), the process returns to step S15, and the similar process is repeated. On the other hand, when it is determined that the operation of terminating the movie recording has been performed (Yes in step S18), the movie recording is terminated and the movie is stored (step S19).

Next, when the TIC analysis is performed, the recorded movie is read (step S20), and the ROI for TIC analysis is set to the region of interest from the read movie (step S21). When the operation of starting the TIC analysis is inputted through the input section 6, the TIC analysis is started, and the positional deviation of the ROI for TIC analysis is automatically corrected by the second position correction section 13 (step S22).

In the process in step S22, the contour of the region of interest in the scanning plane is extracted, and the position of the ROI for TIC analysis is automatically corrected in synchronization with the movement of the region of interest. Finally, the temporal variation of the contrast luminance in the ROI for TIC analysis is calculated, and the calculated temporal variation of the contrast luminance is displayed with, for example, a graph (step S23). Thus, the process is completed.

Figure 4:
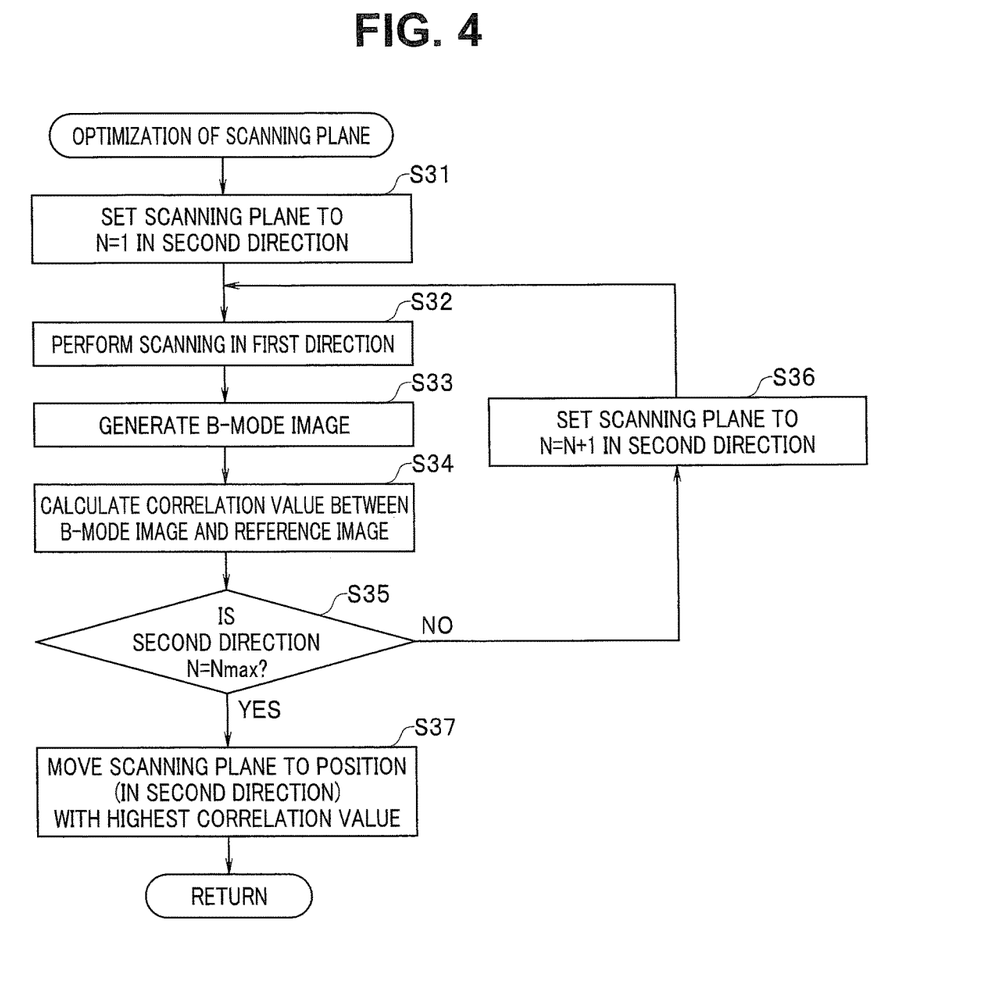
FIG. 4 is a flowchart for explaining an example flow of optimization process of a scanning plane in steps S4 and S15.

Here, the optimization process of the scanning plane in steps S4 and S15 is described with reference to FIG. 4. FIG. 4 is a flowchart for explaining an example flow of the optimization process of the scanning plane in steps S4 and S15.

First, the scanning plane is set to one end (N=1) of the scanning range in a second direction of the ultrasound probe 2 (step S31). Next, the scanning is performed in the first direction (step S32), and the B-mode image is generated by the B-mode image data generation section 17 (step S33). Next, a correlation value between the generated B-mode image and the reference image held by the reference image storage section 16 is calculated by the correlation calculation section 14 (step S34).

Next, it is determined whether the scanning range has been scanned at all positions (N=Nmax) in the second direction (step S35). When the scanning range has not been scanned at all positions (N=Nmax) in the second direction (No in step S35), the scanning plane is moved toward the other end in the second direction of the ultrasound probe 2 by a predetermined value (N=N+1) and set (step S36). Then, the process returns to step S32, and the similar process is repeated to calculate the correlation value between the B-mode image and the reference image.

These processes are repeated until scanning of the scanning range at all positions (N=Nmax) in the second direction is completed. When it is determined that the scanning range has been scanned at all positions (N=Nmax) in the second direction (Yes in step S35), the scanning plane is moved, by the first position correction section 12, to a position having the highest calculated correlation value (step S37). When the process in step S37 is competed and the optimum scanning plane is determined, the process returns to step S5 in FIG. 2 or step S16 in FIG. 3, and the scanning is performed on the optimum scanning plane.

Even if the region of interest is deviated, due to pulsation, hand shake, or other factors, from the region of interest desired to be subjected to the TIC analysis, the above-described processes make it possible to automatically correct the region of interest desired to be subjected to the TIC analysis according to the deviation of the region of interest. In addition, the volume data of the B-mode image generated by the B-mode image data generation section 17 is not stored in the movie storage section 15 and is used only for the position correction of the scanning plane. As a result, the ultrasound observation apparatus 1 makes it possible to three-dimensionally correct the deviation of the region of interest due to pulsation, hand shake, or other factors while suppressing the data capacity, which allows for accurate observation of the region of interest and accurate comprehension of the calculation results of TIC analysis.

Therefore, the ultrasound observation apparatus of the present embodiment allows for accurate comprehension of the temporal variation of the contrast luminance even if the probe is deviated from the region of interest, while suppressing the data capacity for the TIC analysis.

Second Embodiment

Next, a second embodiment is described.

Figure 5:
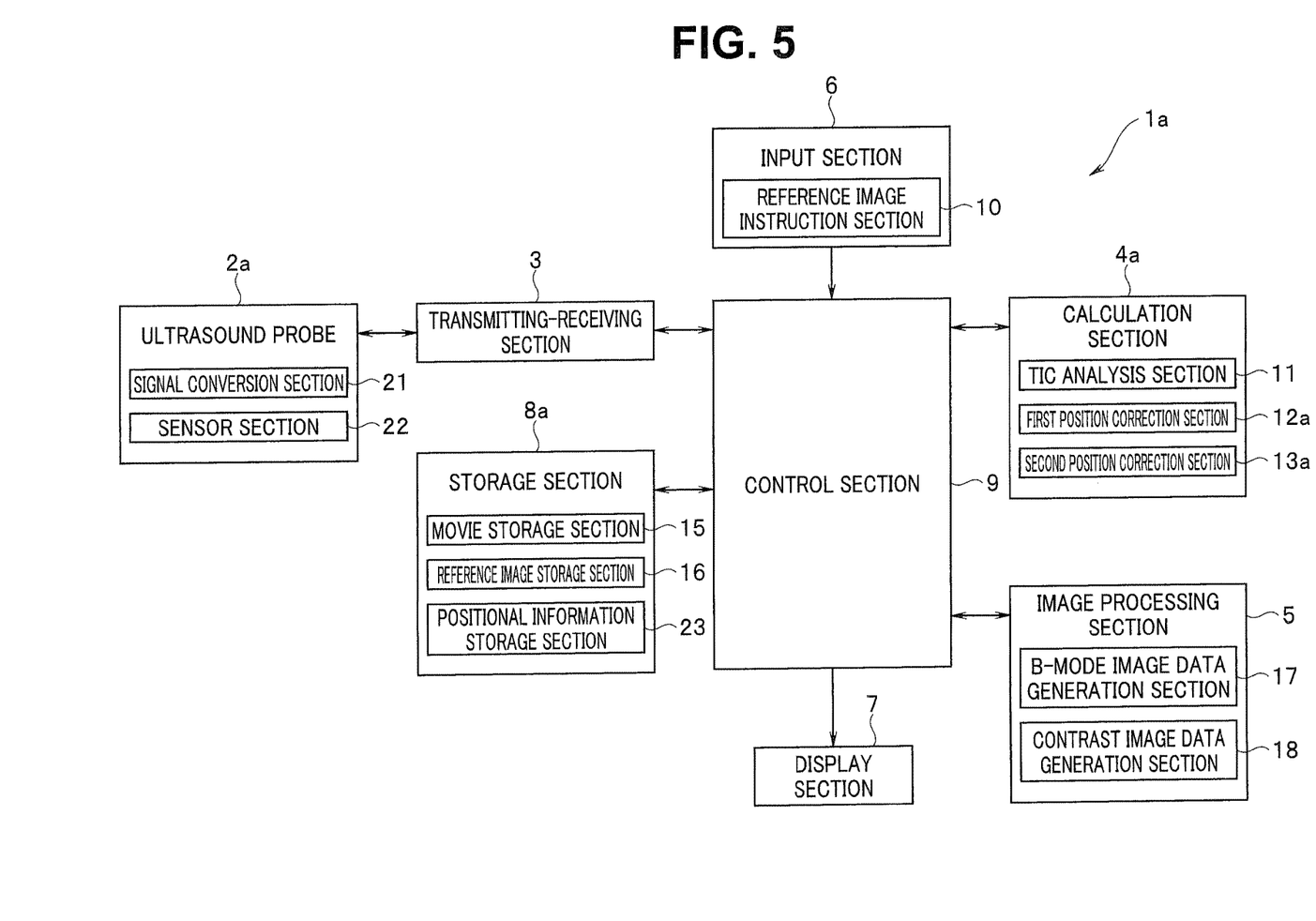
FIG. 5 is a block diagram illustrating an entire configuration of an ultrasound observation apparatus according to a second embodiment.

FIG. 5 is a block diagram illustrating an entire configuration of an ultrasound observation apparatus according to a second embodiment. Note that, in FIG. 5, components similar to components of FIG. 1 are denoted by the same reference numerals and description of the components is omitted.

As illustrated in FIG. 5, an ultrasound observation apparatus 1a includes an ultrasound probe 2a, a calculation section 4a, and a storage section 8a, in place of the ultrasound probe 2, the calculation section 4, and the storage section 8, respectively, of the ultrasound observation apparatus 1 in FIG. 1.

The ultrasound probe 2a is configured by adding a signal conversion section 21 and a sensor section 22 to the ultrasound probe 2 in FIG. 1. Also, in the calculation section 4a, a first position correction section 12a and a second position correction section 13 a are provided in place of the first position correction section 12 and the second position correction section 13, respectively, of the calculation section 4 in FIG. 1, and the correlation calculation section 14 in FIG. 1 is removed. Further, the storage section 8a is configured by adding a positional information storage section 23 to the storage section 8 in FIG. 1.

The signal conversion section 21 converts the electric pulse signal that is received from the transmitting-receiving section 3, into the ultrasound pulse, and converts the ultrasound echo that is reflected by the outside subject, into the electric echo signal again.

The sensor section 22 may be configured of, for example, a gyro sensor or a magnetic sensor, and detects information of the position and the direction of the ultrasound probe 2a. The information of the position and the direction of the ultrasound probe 2a detected by the sensor section 22 is provided to the storage section 8a through the control section 9.

The positional information storage section 23 of the storage section 8a holds positional information in acquisition of the reference image, and holds the information of the position and the direction of the ultrasound probe 2a detected by the sensor section 22 as needed.

The first position correction section 12a corrects deviation of the scanning plane with respect to movement of the region of interest for TIC analysis. At this time, the first position correction section 12a moves the scanning plane based on the information of the position and the direction of the ultrasound probe 2a that is held by the positional information storage section 23.

Also, the second position correction section 13a automatically corrects the position of the ROI for TIC analysis in synchronization with the movement of the region of interest in the scanning plane. At this time, the second position correction section 13a automatically corrects the position of the ROI in the scanning plane, based on the information of the position and the direction of the ultrasound probe 2a that is held by the positional information storage section 23. The other components are similar to components of the first embodiment.

Next, the operation of the ultrasound observation apparatus 1a having such a configuration is described. The process when the TIC analysis is not performed and the process when the TIC analysis is performed are substantially similar to those in FIG. 2 to FIG. 4, and only different processes are described.

In the second embodiment, the optimization process of the scanning plane in step S4 of FIG. 2 and in step S15 of FIG. 3 is different from that of the first embodiment. In the second embodiment, the position and the direction of the ultrasound probe 2a are acquired by the sensor section 22 provided in the ultrasound probe 2a. Then, the first position correction section 12a detects movement degree and a movement direction of the reference image, from the acquired position and the acquired direction of the ultrasound probe 2, thereby correcting the scanning plane from the volume data, based on the detected information, to continuously display the reference image.

Also, in the second embodiment, the process of automatically correcting the ROI for TIC analysis in step S22 of FIG. 3 is different from process of the first embodiment. In the second embodiment, the information of the position and the direction that is detected by the sensor section 22 provided in the ultrasound probe 2a is read out from the positional information storage section 23, and the second position correction section 13a automatically corrects the position of the ROI for TIC analysis, based on the read information of the position and the direction. Other processes are similar to processes in FIG. 2 to FIG. 4.

Figure 6A:
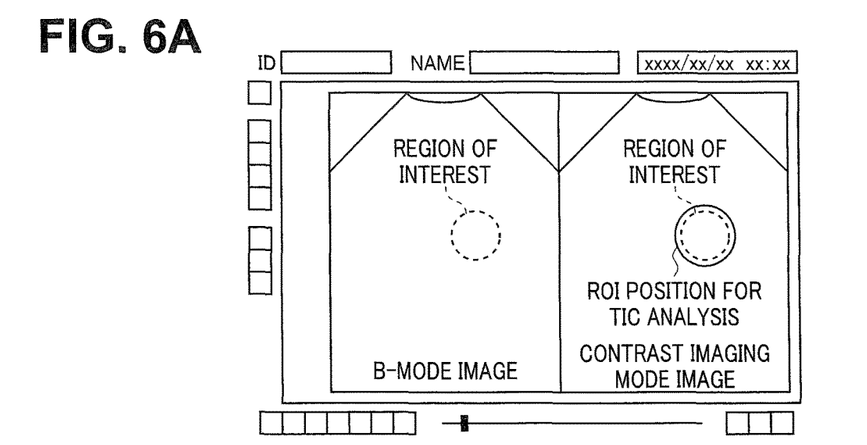
FIG. 6A is a diagram for explaining automatic correction of a position of a ROI for TIC analysis.
Figure 6B:
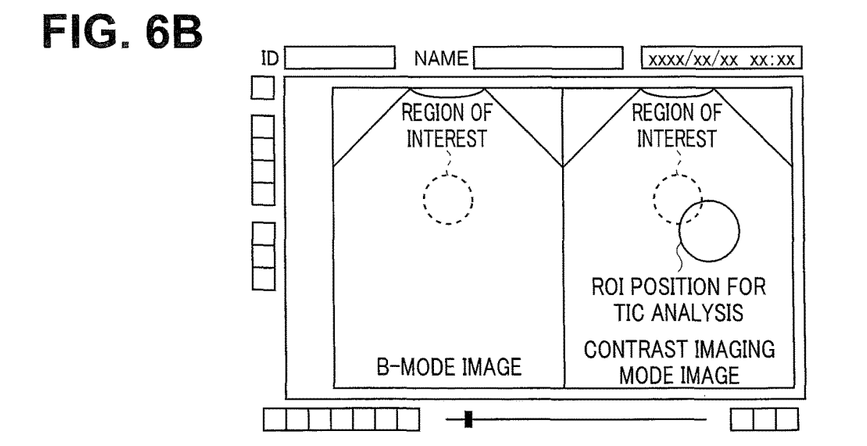
FIG. 6B is a diagram for explaining the automatic correction of the position of the ROI for TIC analysis.
Figure 6C:
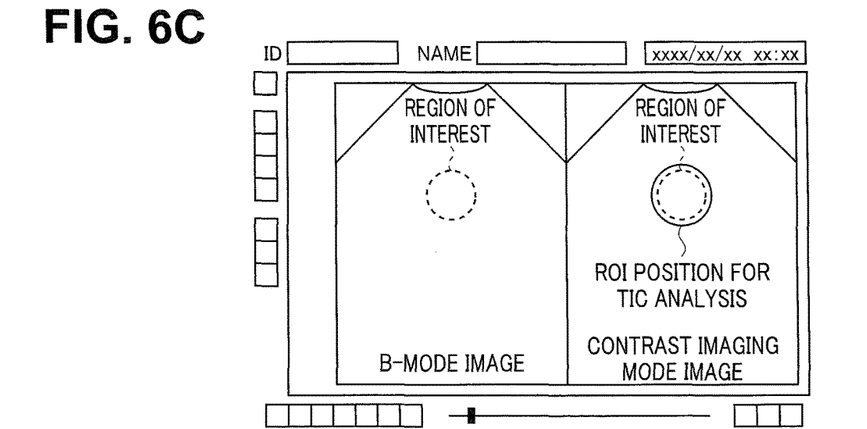
FIG. 6C is a diagram for explaining the automatic correction of the position of the ROI for TIC analysis.

Here, the automatic correction of the position of the ROI for TIC analysis is described with reference to FIG. 6A to FIG. 6C. FIG. 6A to FIG. 6C are diagrams for explaining the automatic correction of the position of the ROI for TIC analysis.

First, as illustrated in FIG. 6A, the ROI for TIC analysis is set to a region of interest in the scanning plane. If the position or the direction of the probe is deviated due to hand shake or other factors, the region of interest is deviated to the outside of the ROI for TIC analysis, as illustrated in FIG. 6B.

In this case, as illustrated in FIG. 6C, the second position correction section 13a automatically corrects the position of the ROI for TIC analysis, based on the information of the position and the direction of the ultrasound probe 2a that is detected by the sensor section 22 and is held by the positional information storage section 23.

As mentioned above, the ultrasound observation apparatus 1a according to the present embodiment is different in the method of optimizing the scanning plane and the method of automatically correcting the position of the ROI for TIC analysis from the first embodiment. In the ultrasound observation apparatus 1a according to the present embodiment, the sensor section 22 is provided in the ultrasound probe 2a to acquire the information of the position and the direction of the ultrasound probe 2a, and the scanning plane is optimized and the position of the ROI for TIC analysis is automatically corrected based on the information.

Other components and operation are similar to the components and the operation of the first embodiment. Therefore, the ultrasound observation apparatus 1a of the present embodiment allows for accurate comprehension of the temporal variation of the contrast luminance even if the probe is deviated from the region of interest, while suppressing the data capacity for the TIC analysis, as with the first embodiment.

Third Embodiment

Next, a third embodiment is described.

The display section 7 displays the various kinds of information including the image generated by the image processing section 5. The image displayed on the display section 7 is a live image that is being observed. An image that has the highest correlation value with the reference image (the movie for TIC analysis) is stored in the apparatus (for example, stored in the movie storage section 15), and is read out and used in the TIC analysis. Other components are similar to components of the first or second embodiment.

Fourth Embodiment

Next, a fourth embodiment is described.

The display section 7 displays the various kinds of information including the image generated by the image processing section 5. The image displayed on the display section 7 is an image (a movie for TIC analysis) that has the highest correlation value with the reference image, calculated by the correlation calculation section 14. Note that the display section 7 may display the image that has the highest correlation value with the reference image and the live image being observed at a time. At this time, only the image that has the highest correlation value with the reference image by the correlation calculation section 14 is stored in the apparatus as the movie for TIC analysis. Other components are similar to components of the first or second embodiment.

Note that in the third embodiment and the fourth embodiment, the volume data of the B-mode image that is generated for the correlation calculation by the B-mode image data generation section 17 may be displayed on the display section 7, together with the image that has the highest correlation value with the reference image and/or the live image being observed, at a time.

Note that the respective steps in the respective flowcharts in the present specification may be changed in execution order, executed together at a time, or executed in different order in each execution, unless contrary to the nature of the steps.

The present invention is not limited to the above-described embodiments, and other various modifications and alternations may occur within the scope of the present invention.

What is claimed is:

1. An ultrasound observation apparatus that sets a second region of interest for analysis of temporal variation of luminance to a first region of interest and calculates the temporal variation of the luminance in the second region of interest, the ultrasound observation apparatus comprising:
   an ultrasound probe configured to change a transmitting-receiving direction of ultrasound in a first direction and a second direction to perform two-dimensional scanning with an ultrasound beam;
   a transmitting-receiving circuit configured to control the transmitting-receiving direction of the ultrasound beam of the ultrasound probe;
   an image processing circuit configured to generate volume data of a B-mode image from a result of scanning with the ultrasound beam in the first direction and the second direction;
   a user interface configured to set, as a reference image, an image in which the first region of interest is clearly visualized;
   a first memory configured to hold the reference image;
   a first position correction circuit configured to correct a scanning plane to allow an image of the volume data similar to the reference image that is set by the user interface, to be constantly displayed;
   a second memory configured to hold a movie obtained by transmitting and receiving the ultrasound beam to/from only the scanning plane that is corrected by the first position correction circuit;
   a TIC (time intensity curve) analysis circuit configured to calculate temporal variation of contrast luminance in the second region of interest that is set to the first region of interest;
   a second position correction circuit configured to automatically correct the position of the second region of interest for TIC analysis, in synchronization with movement of the first region of interest in the scanning plane held by the second memory;
   a sensor provided in the ultrasound probe, and configured to detect a position and a direction of the ultrasound probe; and
   a third memory configured to hold information of the position and the direction of the ultrasound probe detected by the sensor,
   wherein the first position correction circuit automatically corrects, based on the information of the position and the direction of the ultrasound probe that is read from the third memory, the scanning plane to allow the reference image held by the first memory to be constantly displayed, wherein the second position correction circuit automatically corrects the position of the second region of interest, based on the information of the position and the direction of the ultrasound probe that is read from the third memory, and wherein the transmitting-receiving circuit further controls an output of the ultrasound beam to allow an output of the ultrasound beam in acquisition of temporal variation data of the contrast luminance to be larger than an output of the ultrasound beam in acquisition of the volume data.

2. The ultrasound observation apparatus according to claim 1, wherein the first position correction circuit calculates a correlation value between the volume data and the reference image held by the first memory, and wherein the transmitting-receiving circuit moves the scanning plane in the second direction to maximize the correlation value.

3. The ultrasound observation apparatus according to claim 1, wherein the second position correction circuit performs contour extraction of the first region of interest to automatically correct the position of the second region of interest, in synchronization with the movement of the first region of interest.

4. The ultrasound observation apparatus according to claim 1, wherein the sensor is a gyro sensor or a magnetic sensor.

5. An operation method for an ultrasound observation apparatus, in which a second region of interest is set for analysis of temporal variation of luminance to a first region of interest so as to calculate the temporal variation of the luminance in the second region of interest, the operation method comprising:

a step of causing, by a computer, an ultrasound probe to perform two-dimensional scanning with an ultrasound beam by changing a transmitting-receiving direction of ultrasound in a first direction and a second direction;

a step of controlling, by the computer, the transmitting-receiving direction of the ultrasound beam of the ultrasound probe;

a step of generating, by the computer, volume data of a B-mode image from a result of scanning with the ultrasound beam in the first direction and the second direction;

a step of setting, by the computer, an image in which the first region of interest is clearly visualized, as a reference image;

a step of holding, by the computer, the reference image in a first memory;

a step of correcting, by the computer, a scanning plane to allow an image of the volume data similar to the reference image, to be constantly displayed;

a step of holding, by the computer, a movie obtained by transmitting and receiving the ultrasound beam to/from only the scanning plane that is corrected, in a second memory;

a step of calculating, by the computer, temporal variation of contrast luminance in the second region of interest that is set to the first region of interest;

a step of automatically correcting, by the computer, the position of the second region of interest for TIC (time intensity curve) analysis, in synchronization with movement of the first region of interest in the scanning plane held by the second memory;

a step of detecting, by the computer, a position and a direction of the ultrasound probe;

a step of holding, by the computer, information of the detected position and the detected direction of the ultrasound probe, in a third memory;

a step of automatically correcting, by the computer, based on the information of the position and the direction of the ultrasound probe that is read from the third memory, the scanning plane to allow the reference image held by the first memory to be constantly displayed;

a step of automatically correcting, by the computer, the position of the second region of interest, based on the information of the position and the direction of the ultrasound probe that is read from the third memory; and a step of controlling, by the computer, an output of the ultrasound beam to allow an output of the ultrasound beam in acquisition of temporal variation data of the contrast luminance to be larger than an output of the ultrasound beam in acquisition of the volume data.

* * * * *